(12) United States Patent
Flory

(10) Patent No.: US 7,410,564 B2
(45) Date of Patent: Aug. 12, 2008

(54) APPARATUS AND METHOD FOR BIOPOLYMER IDENTIFICATION DURING TRANSLOCATION THROUGH A NANOPORE

(75) Inventor: Curt A. Flory, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 268 days.

(21) Appl. No.: 10/352,675

(22) Filed: Jan. 27, 2003

(65) Prior Publication Data

US 2004/0144658 A1 Jul. 29, 2004

(51) Int. Cl.
*G01N 27/327* (2006.01)
(52) U.S. Cl. ............... 205/777.5; 205/775; 204/403.01; 204/403.06
(58) Field of Classification Search ......... 204/601–605, 204/451–455, 409, 403.01; 205/775, 777.5
See application file for complete search history.

(56) References Cited

U.S. PATENT DOCUMENTS

| 6,627,067 | B1 | 9/2003 | Branton et al. | |
| 7,033,476 | B2 * | 4/2006 | Lee et al. | ................... 204/603 |
| 2002/0197618 | A1 | 12/2002 | Sampson | |

FOREIGN PATENT DOCUMENTS

WO  WO 03/000920 A2  1/2003

OTHER PUBLICATIONS

Caplus abstract of Hoffman et al. (Possible correlation between the effects of some carcinogenic agents and electronic structure of deoxyribonucleic acid (DNA) Cancer Research (1961), 21, 474-84).*
Caplus abstract of Hari et al. ("p-Electrons in a single strand of DNA: a phenomenological approach," International Journal of Modern Physics B: Condensed Mater Physics, Statistical Physics, Applied Physics (2004), 18(13), 1845-1910).*
Caplus abstract of Ladik ("Energy bands in DNA," Studia Biophysica (1968), 8, 87-98), Ladik.*
Wolf ("Electron tunneling spectroscopy," Rep. Prog. Phys., vol. 41, 1978, pp. 1440-1508).*
Whitman (Tunneling Microscopy and Spectroscopy, to appear in The Encyclopedia of Applied Physcis (VCH), Feb. 7, 1997, pp. 01-23).*
Li et al., "Ion-Beam Sculpting at Nanometre Length Scales", (2001), Macmillan Magazines Ltd., vol. 412, pp. 166-169.

(Continued)

*Primary Examiner*—Alex Noguerola

(57) ABSTRACT

The present invention provides an apparatus and method for identifying and sequencing a biopolymer translocating a nanopore. The apparatus of the present invention provides a first electrode, a second electrode and a potential means for applying a bias ramping potential across the electrodes to produce resonant tunneling of current carriers between the two electrodes. As the bias potential is ramped across the electrodes the increase in tunneling current occurs as the carrier energy sequentially matches the conduction band energies of the translocating biopolymer. This technique allows for real-time identification and sequencing of a biopolymer as the band energy spectra of the individual portions of the bipolymer are recorded, differentiated and identified. A method for identifying the biopolymer is also disclosed.

26 Claims, 8 Drawing Sheets

OTHER PUBLICATIONS

Akeson et al., "Microsecond Time-Scale Discrimination among Polcytidylic Acid, Poladenylic Acid, and Polyurdylic Acid as Homopolymers or as Segments within Single RNA Molecules", (1999), Biophysical Journal, vol. 77, pp. 3227-3233.

Kasianowicz et al., "Characterization of Individual Polynucleotide Molecules using a Membrane Channel", (1996), Proc. Natl. Acad. Sci. USA, vol. 93, pp. 13770-13773.

European Search Report Dated: Jan 26, 2004, for Application No. EP03028286.

* cited by examiner

Bias A
$(E = E_4)$

Bias B
$(E = E_3)$

Bias C
$(E = E_2)$

APPARATUS AND METHOD FOR BIOPOLYMER IDENTIFICATION DURING TRANSLOCATION THROUGH A NANOPORE

TECHNICAL FIELD

The invention relates generally to the field of biopolymers and more particularly to an apparatus and method for biopolymer sequencing and identification using nanopore structures.

BACKGROUND

Manipulating matter at the nanometre scale is important for many electronic, chemical and biological advances (See Li et al., "Ion beam sculpting at nanometer length scales", *Nature,* 412: 166-169, 2001). A number of sequencing techniques have been proposed at the micrometer and nanometer scale in response to the human genome project. These techniques have been largely developed to help characterize and understand expression of genes in vivo. A popular technique uses micro arrays and hybridization of cDNA to determine the presence or absence of a particular target gene. A target gene and probe are exposed in solution and bind if relative hybridization sequences match. Hybridization is indicative of the presence of the sequence or target gene. A dye may be employed with the target or probe to then determine existence and efficiency of hybridizations. The technique has been extended for use in determining the presence of single nucleotide polymorphism (SNP'S) in target cDNA. Micro arrays provide the promise of being able to accurately and concurrently screen for a variety of diseases in a particular patient. Theoretically, a patient should be able to enter a hospital, have blood taken, DNA extracted and genes sequenced. The sequencing methods provide for a genetic blue print of the individual. This provides patient specific information to doctors regarding susceptibility towards disease or existence of genetic abnormalities. A few major drawbacks of the micro array technique concerns difficulty in manufacturing as well as the long time for effective hybridizations between probe and target (generally overnight to maintain high specificity). In addition, the large amounts of genomic DNA in a patient would require an inordinate amount of time and work. Therefore, new techniques are now being explored to more quickly sequence biopolymers. Systems that are on the nanoscale are both effective on resources (limited materials), but also may more closely mimic the processes already present in living cells (i.e. translocation processes). Therefore, nanopore technology has become a fundamental field area of interest to molecular biologists and biochemists alike.

It has been demonstrated that a voltage gradient can drive single-stranded biopolymers through a transmembrane channel, or nanopore (See Kasianowicz et al., "Characterization of individual polynucleotide molecules using a membrane channel", *Proc. Natl. Acad. Sci. USA,* 93: 13770-13773, 1996). During the translocation process, the extended biopolymer molecule will block a substantial portion of the otherwise open nanopore channel. This blockage leads to a decrease in the ionic current flow of the buffer solution through the nanopore during the biopolymer translocation. The passage of a single biopolymer can be monitored by recording the translocation duration and the blockage current, yielding plots with predictable stochastic sensing patterns. From the uniformly controlled translocation conditions, the lengths of the individual biopolymers can be determined from the translocation time. Furthermore, the differing physical and chemical properties of the individual monomers of the biopolymer strand may generate a measurable and reproducible modulation of the blockage current that allows an identification of the specific monomer sequence of the translocating biopolymer. These initially proposed systems suffer from a number of problems. For instance, some of the proposed systems required the self-assembly of pore forming proteins on membranes (i.e. α-hemolysin). Reproducibility of membranes and systems has been quite problematic. Secondly, commercial products require robustness not present in sensitive systems that require fluctuations of ionic currents for measurements. For these reasons, recent research has focused more on solid-state pore techniques that have an ability for high reproducibility and ease of fabrication. Such techniques as "ion beam sculpting" have shown some promise in fabricating molecular scale holes and nanopores in thin insulating solid-state membranes. These pores have also been effective in localizing molecular-scale electrical junctions and switches (See Li et al., "Ion beam sculpting at nanometer length scales", *Nature,* 412: 166-169, 2001).

These techniques have shown similar consistent results and current blockage with double stranded DNA reminiscent of ionic current blockages observed when single stranded DNA are translocated through the channel formed by α-hemolysin in a lipid bilayer. The duration of these blockages have been on the millisecond scale and current reductions have been to 88% of the open-pore value. This is commensurate with translocation of a rod-like molecule whose cross-sectional area is 3-4 nm$^2$ (See Li et al., "Ion beam sculpting at nanometer length scales", *Nature,* 412: 166-169, 2001). This methodology, however, suffers from the limitation that only crude measurements of the presence or absence of the translocating polymer can be made. In addition, these systems are incapable of actually determining the primary sequences (order of monomeric units) of the translocating biopolymer.

A second approach has been suggested for detecting a biopolymer translocating a nanopore in a solid-state material such as $Si_3N_4$. However, it is well known that the tunneling current has an exponential dependence upon the height and width of the quantum mechanical potential barrier to the tunneling process. This dependence implies an extreme sensitivity to the precise location in the pore of the translocating molecule. Both steric attributes and physical proximity to the tunneling electrode could cause changes in the magnitude of the tunneling current which would be far in excess of the innate differences expected between different base-types under ideal conditions. For this reason, it is difficult to expect the simplest tunneling configurations to have the specificity required to perform sequencing.

For these reasons, there is a need for improved systems and methods that quickly and efficiently sequence translocating biopolymers in solid-state systems with high reproducibility and predictability. These and other problems with the prior art processes and designs are obviated by the present invention. The references cited in this application infra and supra, are hereby incorporated in this application by reference. However, cited references or art are not admitted to be prior art to this application.

SUMMARY OF THE INVENTION

The invention provides a method and apparatus for improved identification and sequencing of biopolymers. The apparatus and method may be used for detecting a biopolymer or a portion of a biopolymer translocating through a nanopore. The apparatus comprises a first electrode, a second electrode, and a potential means for applying a ramping bias potential across the first and second electrodes. The second electrode is spaced from the first electrode to define a nanopore between the first and second electrodes. The potential means for applying the ramping bias potential produces a signal indicative of a portion of the biopolymer translocating the nanopore. The invention takes advantage of resonant tunneling processes during electrode voltage scan which allows the double barrier tunneling potential to be dynamically symmetrized.

The invention also provides a method for identifying a biopolymer in a nanopore defined between a first and second electrode. The method comprises applying an electrical current from a first electrode through a portion of a biopolymer to a second electrode to produce a signal indicative of a portion of the biopolymer positioned in the nanopore.

BRIEF DESCRIPTION OF THE FIGURES

The invention is described in detail below with reference to the following figures.

DETAILED DESCRIPTION OF THE INVENTION

Figure 1A:
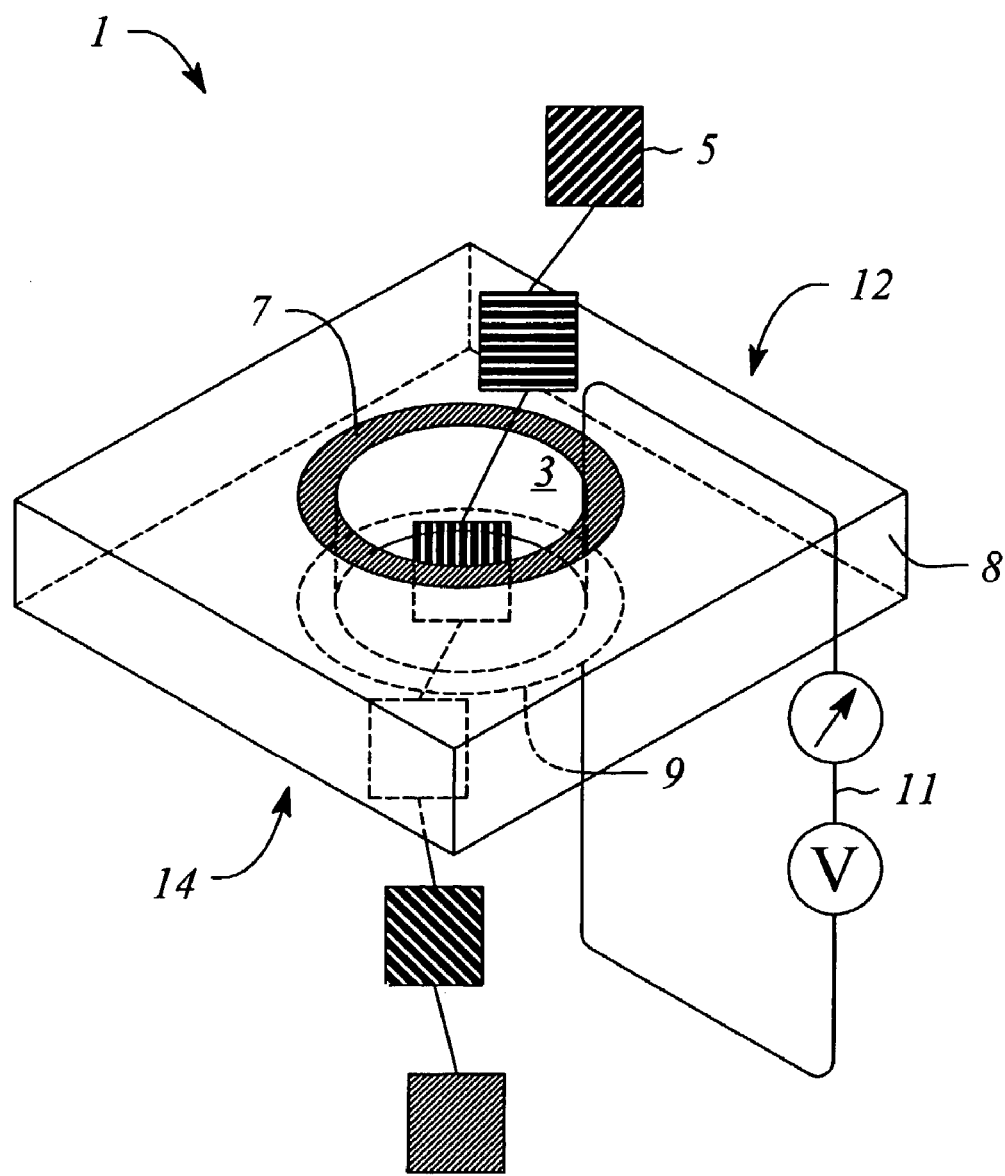
FIG. 1A shows a schematic representation of a proposed double-ring electrode structure and measurement system that allows individual monomer detection through resonant tunneling during electrode voltage scan.

Before describing the present invention in detail, it is to be understood that this invention is not limited to specific compositions, method steps, or equipment, as such may vary. It is also to be understood that the terminology used herein is for the purpose of describing particular embodiments only, and is not intended to be limiting. Methods recited herein may be carried out in any order of the recited events that is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

Unless defined otherwise below, all technical and scientific terms used herein have the same meaning as commonly understood by one of ordinary skill in the art to which this invention belongs. Still, certain elements are defined herein for the sake of clarity.

It must be noted that, as used in this specification and the appended claims, the singular forms "a", "an" and "the" include plural referents unless the context clearly dictates otherwise. Thus, for example, reference to "a biopolymer" includes more than one biopolymer, and reference to "a potential means " includes a plurality of potential means and the like. In describing and claiming the present invention, the following terminology will be used in accordance with the definitions set out below.

A "biopolymer" is a polymer of one or more types of repeating units. Biopolymers are typically found in biological systems and particularly include polysaccharides (such as carbohydrates), peptides (which term is used to include polypeptides and proteins), glycans, proteoglycans, lipids, sphingolipids, known biologicals materials such as antibodies, etc. and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in hydrogen bonding interactions, such as Watson-Crick type, Wobble type and the like. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

A "substrate" refers to any surface that may or may not be solid and which is capable of holding, embedding, attaching or which may comprise the whole or portions of an electrode.

"Hybridizing", "annealing" and "binding", with respect to polynucleotides, are used interchangeably. "Binding efficiency" refers to the productivity of a binding reaction, measured as either the absolute or relative yield of binding product formed under a given set of conditions in a given amount of time. "Hybridization efficiency" is a particular sub-class of binding efficiency, and refers to binding efficiency in the case where the binding components are polynucleotides. It will also be appreciated that throughout the present application, that words such as "upper", "lower" are used in a relative sense only. A "set" may have one type of member or multiple different types. "Fluid" is used herein to reference a liquid.

The term "resonant" or "resonant tunneling" refers to an effect where the relative energy levels between the current carriers in the electrodes are relatively similar to the energy levels of the proximal biopolymer segment. This provides for increased conductivity.

The term "tunneling" refers to the ability of an electron to move from a first position in space to a second position in space through a region that would be energetically excluded without quantum mechanical tunneling.

The term "in" refers to being "within" and/or a portion that may also be exterior to. For instance, a biopolymer "in" a nanopore may mean that the whole biopolymer is within the opening of the nanopore or only a small portion of the biopolymer is located near the nanopore with a substantial portion protruding exterior to the nanopore.

The term "symmetric" or "symmetrized" refers to similar tunneling barriers adjacent to both electrodes.

The term "nanopore" refers to any pore or hole between at least a pair of electrodes or a hole in a solid substrate. Nanopores can range in size and can range from 1 nm to around 300 nm. Most effective nanopores have been roughly around 2 nm.

The term "translocation" or to "translocate" refers to movement from one side to another, movement in a defined direction. Any action or biopolymer following along a vector that has velocity and/or direction.

The term "portion" or "portion of a biopolymer" refers to a part, subunit, monomeric unit, portion of a monomeric unit, atom, portion of an atom, cluster of atoms, charge or charged unit.

The term "ramping potential" or "bias potential" refers to having the ability to establish a variety of different voltages over time. In certain cases this may be referred to as "scanning a voltage gradient" or altering a voltage gradient per unit of time. The ramping potential is produced by the "potential means".

The term "voltage gradient" refers to having the ability to establish a potential between any two electrodes.

The term "adjacent" refers to anything that is near, next to or adjoining. For instance, a nanopore may be near an electrode, it may be next to the electrode, it may pass through an electrode or it may be adjoining the electrode. This would include spacing in linear, two-dimensional and three-dimensional space.

Figure 1B:
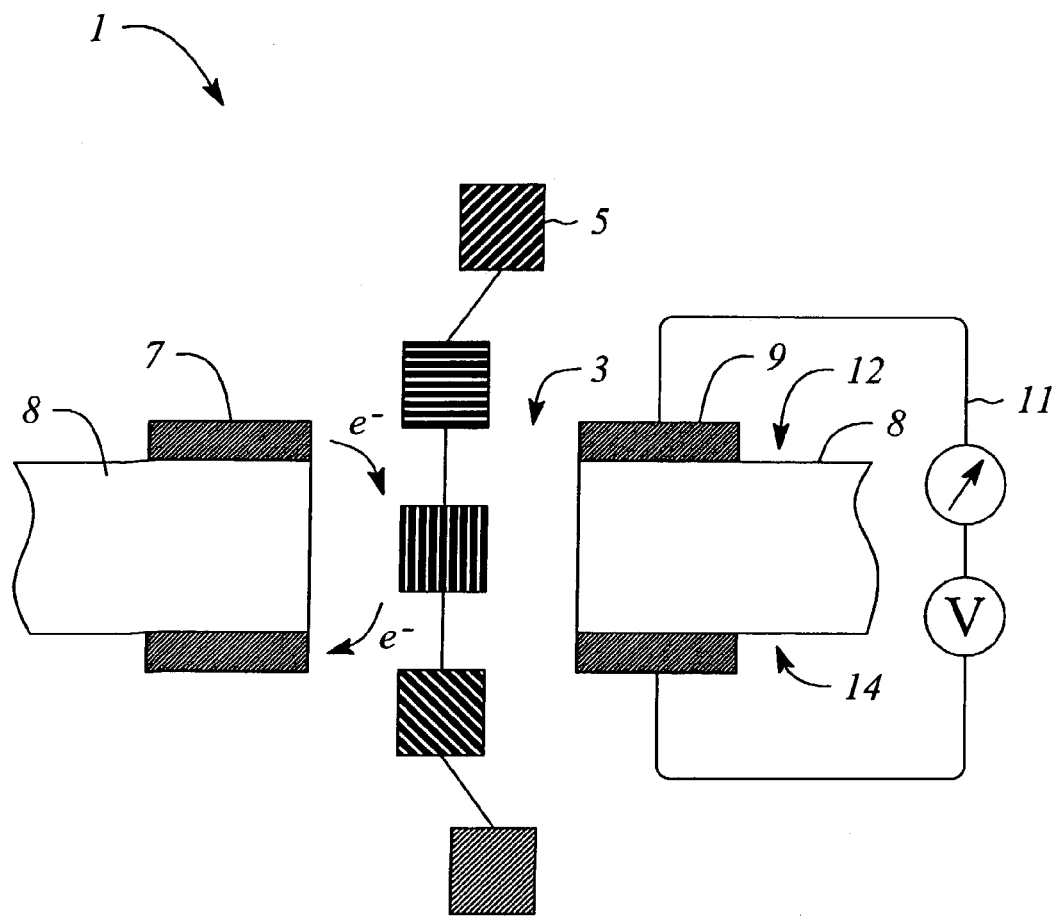
FIG. 1B shows a cross-sectional view of the double-ring electrode structure and measurement system.

Referring now to FIGS. 1-3, the present invention provides a biopolymer identification apparatus 1 that is capable of identifying or sequencing a biopolymer 5. The biopolymer identification apparatus 1 comprises a first electrode 7, a second electrode 9 and a potential means 11. Either or both of the electrodes may be ring shaped. The first electrode 7 and the second electrode 9 are electrically connected to the potential means 11. The second electrode 9 is adjacent to the first electrode 7 and spaced from the first electrode 7. A nanopore 3 may pass through the first electrode 7 and the second electrode 9. However, this is not a requirement of the invention. In the case that the optional substrate 8 is employed, the nanopore 3 may also pass through the substrate 8. Nanopore 3 is designed for receiving a biopolymer 5. The biopolymer 5 may or may not be translocating through the nanopore 3. When the optional substrate 8 is employed, the first electrode 7 and the second electrode 9 may be deposited on the substrate, or may comprise a portion of the substrate 8. In this embodiment of the invention, the nanopore 3 also passes through the optional substrate 8. Other embodiments of the invention may also be possible where the first electrode 7 and the second electrode 9 are positioned in the same plane (as opposed to one electrode being above or below the other) with or without the optional substrate 8. The use of multiple electrodes and/or substrates are also within the scope of the invention.

The biopolymer 5 may comprise a variety of shapes, sizes and materials. The shape or size of the molecule is not important, but it must be capable of translocation through the nanopore 3. For instance, both single stranded and double stranded RNA and DNA may be used as a biopolymer 5. In addition, the biopolymer 5 may contain groups or functional groups that are charged. Furthermore, metals or materials may be added, doped or intercalated within the biopolymer 5 to provide a net dipole, a charge or allow for conductivity through the biomolecule. The material of the biopolymer must allow for electron tunneling between electrodes.

The first electrode 7 may comprise a variety of electrically conductive materials. Such materials include electrically conductive metals and alloys of tin, copper, zinc, iron, magnesium, cobalt, nickel, and vanadium. Other materials well known in the art that provide for electrical conduction may also be employed. When the first electrode 7 is deposited on or comprises a portion of the solid substrate 8, it may be positioned in any location relative to the second electrode 9. It must be positioned in such a manner that a potential can be established between the first electrode 7 and the second electrode 9. In addition, the bipolymer 5 must be positioned sufficiently close so that a portion of it may be identified or sequenced. In other words, the first electrode 7, the second electrode 9, and the nanopore 3 must be spaced and positioned in such a way that the bipolymer 5 may be identified or sequenced. This should not be interpreted to mean that the embodiment shown in FIG. 1 in any way will limit the spatial orientation and positioning of each of the components of the invention. The first electrode 7 may be designed in a variety of shapes and sizes. Other electrode shapes well known in the art may be employed. In addition, parts or curved parts of rings or other shapes may be used with the invention. The electrodes may also be designed in broken format or spaced from each other. However, the design must be capable of establishing a potential across the first electrode 7, and the nanopore 3 to the second electrode 9.

The second electrode 9 may comprise the same or similar materials as described above for the first electrode 7. As discussed above, its shape, size and positioning may be altered relative to the first electrode 7 and the nanopore 3.

The optional substrate 8 may comprise a variety of materials known in the art for designing substrates and nanopores. The substrate 8 may or may not be a solid material. For instance, the substrate 8 may comprise a mesh, wire, or other material that a nanopore may be constructed. Such materials may comprise silicon, silica, solid-state material such as $Si_3N_4$, carbon based materials, plastics, metals, or other materials known in the art for etching or fabricating semiconductor or electrically conducting materials. The solid substrate 8 may comprise various shapes and sizes. However, it must be large enough and of sufficient width to be capable of forming the nanopore 3 through it.

The nanopore 3 may be positioned anywhere on/through the optional substrate 8. As described above, the nanopore 3 may also be established by the spacing between the first electrode 7 and the second electrode 9 (in a planar or non planar arrangement). When the substrate 8 is employed, it should be positioned adjacent to the first electrode 7 and the second electrode 9. The nanopore may range in size from 1 nm to as large as 300 nms. In most cases, effective nanopores for identifying and sequencing biopolymers would be in the range of around 2-20 nm. These size nanopores are just large enough to allow for translocation of a biopolymer. The nanopore 3 may be established using any methods well known in the art. For instance, the nanopore 3, may be sculpted in the substrate 8, using argon ion beam sputtering, etching, photolithography, or other methods and techniques well known in the art.

The potential means 11 may be positioned anywhere relative to the substrate 8, the nanopore 3, the first electrode 7 and the second electrode 9. The potential means 11 should be capable of ramping to establish a voltage gradient between the first electrode 7 and the second electrode 9. A variety of potential means 11 may be employed with the present invention. A number of these potential means are known in the art. The potential means 11 has the ability to ramp to establish a voltage gradient between the first electrode 7 and the second electrode 9. This is an important aspect of the present invention and for this reason is discussed in more detail below.

An optional means for signal detection may be employed to detect the signal produced from the bipolymer and potential means 11. This means for signal detection may be any structure, component or apparatus that is well known in the art and that may be electrically connected to one or more components of the present invention.

Figure 2A:
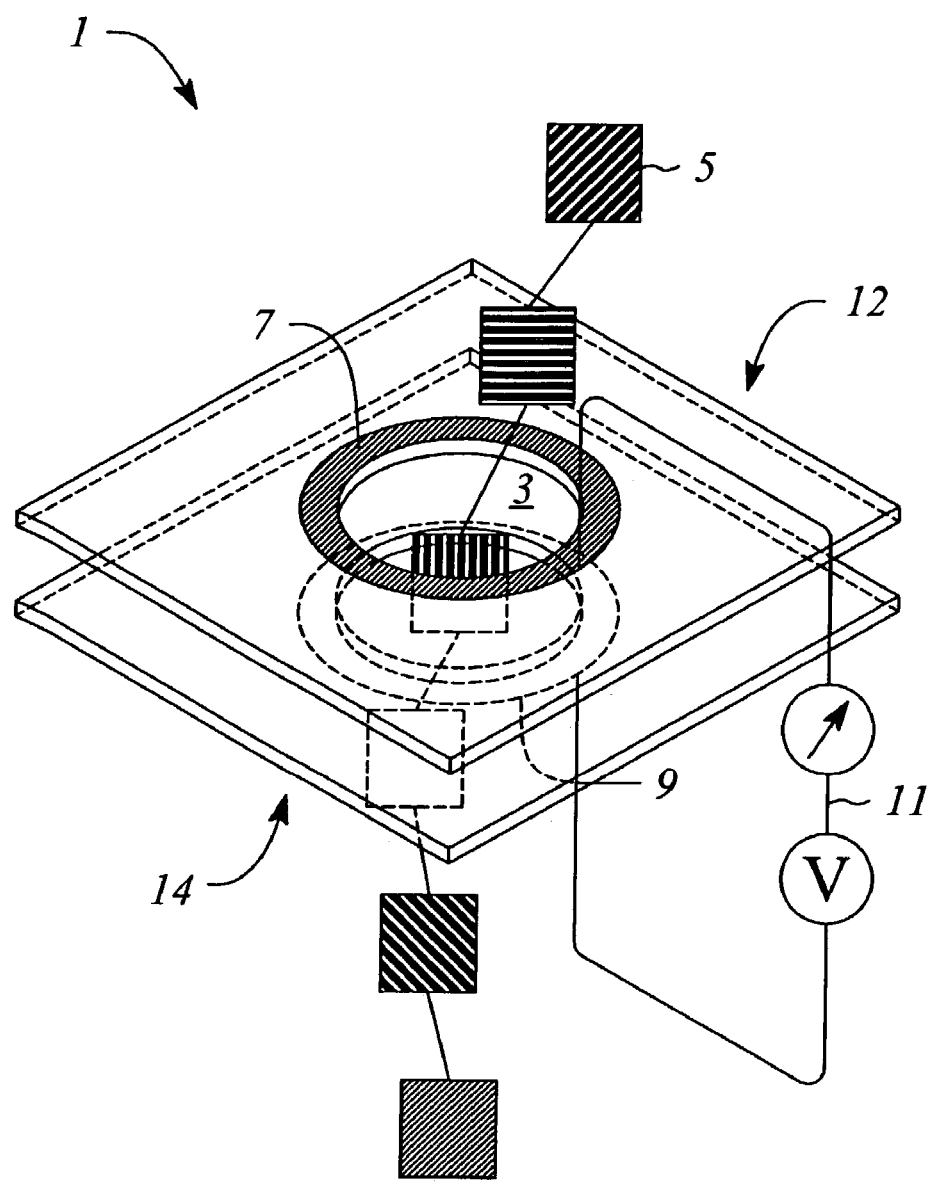
FIG. 2A shows a schematic representation of a second embodiment of the present invention.
Figure 2B:
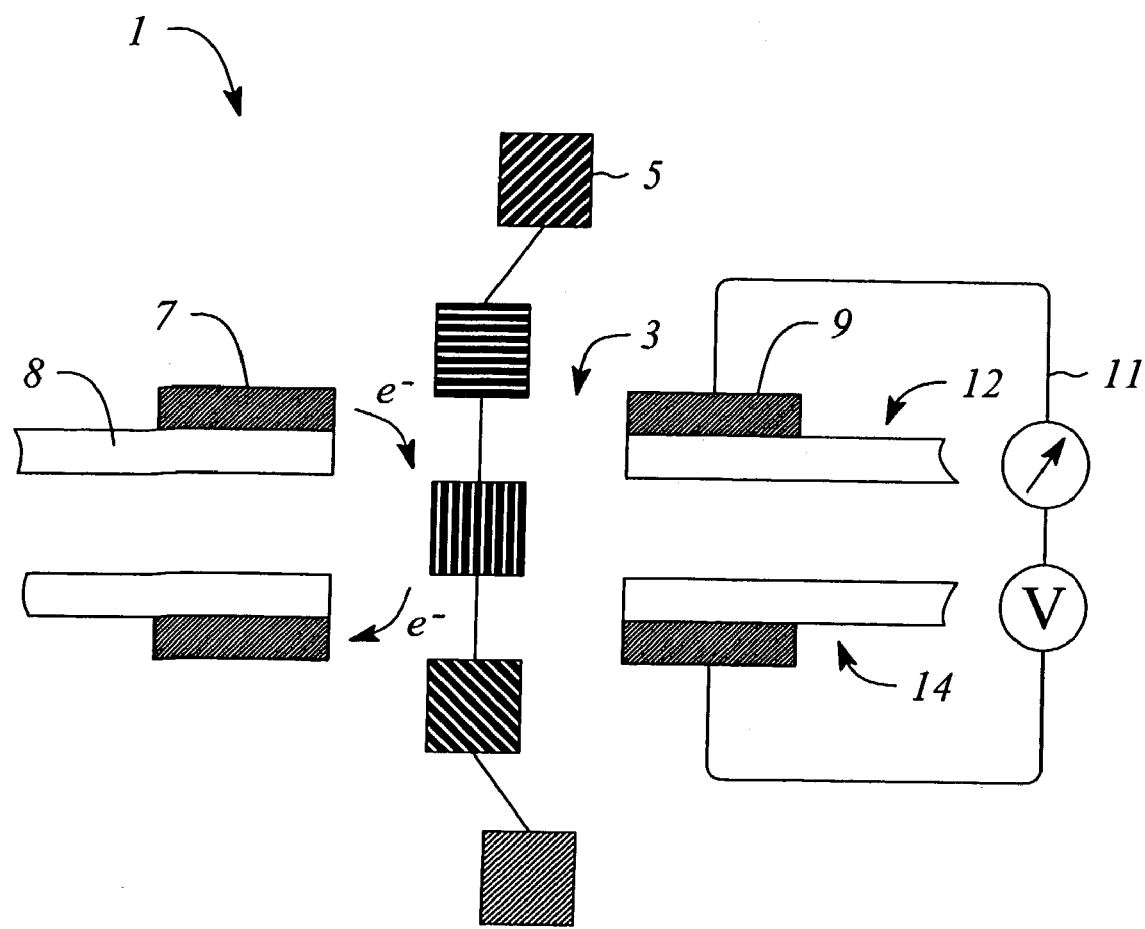
FIG. 2B shows a cross-sectional view of the second embodiment of the present invention.

Referring now to FIGS. 2A and 2B, a second embodiment of the invention, a series of separate substrates may be employed. For instance, a first substrate 16 and a second substrate 18 may be employed in place of the single substrate 8. In this embodiment of the invention, the first electrode 7 comprises first substrate 16 or a portion of this substrate. The electrode may be embedded, attached, layered, deposited, etched on the substrate or it may comprise all or a portion of the first substrate 16. Second electrode 9 comprises the second substrate 18 or a portion of the substrate. The electrode may be embedded, attached, layered, deposited, etched on the substrate or it may comprise all or a portion of the second substrate 18. The first substrate 16 is positioned adjacent to the second substrate 18. The figure shows the first substrate 16 positioned spatially above the second substrate 18. The first electrode 7 may comprise a first nanopore 3 while the second electrode 9 may comprise a second nanopore 3'. The first nanopore 3 of the first electrode 7 and the second nanopore 3' of the second electrode 9 may have center points that are coaxially aligned to form a single contiguous pore that the biopolymer 5 may translocate through. It is within the scope of the invention that the nanopore 3 and the nanopore 3' center points may be offset or spaced at relative angles and distances from each other.

Figure 3A:
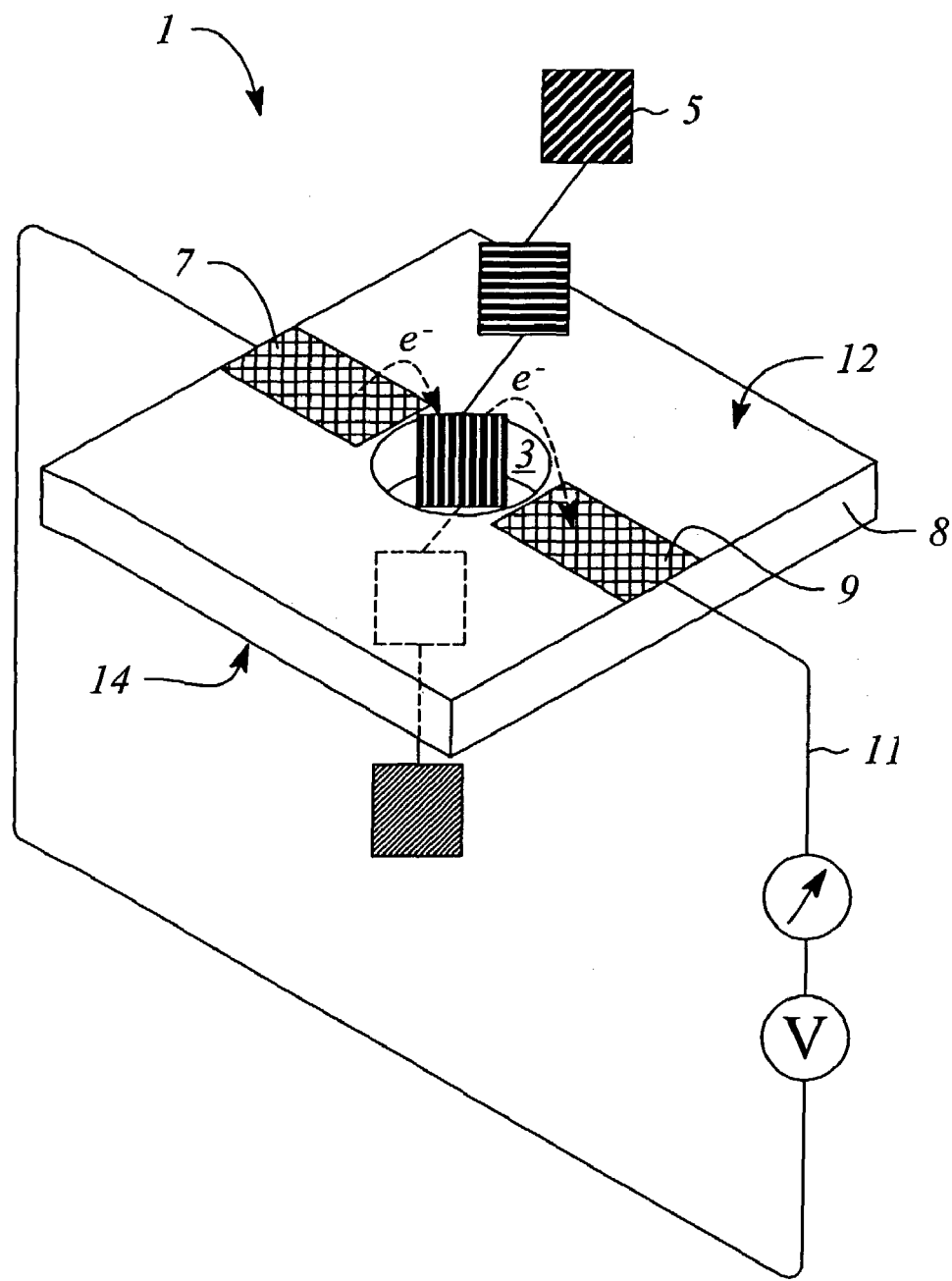
FIG. 3A shows a schematic representation of a third embodiment of the present invention.
Figure 3B:
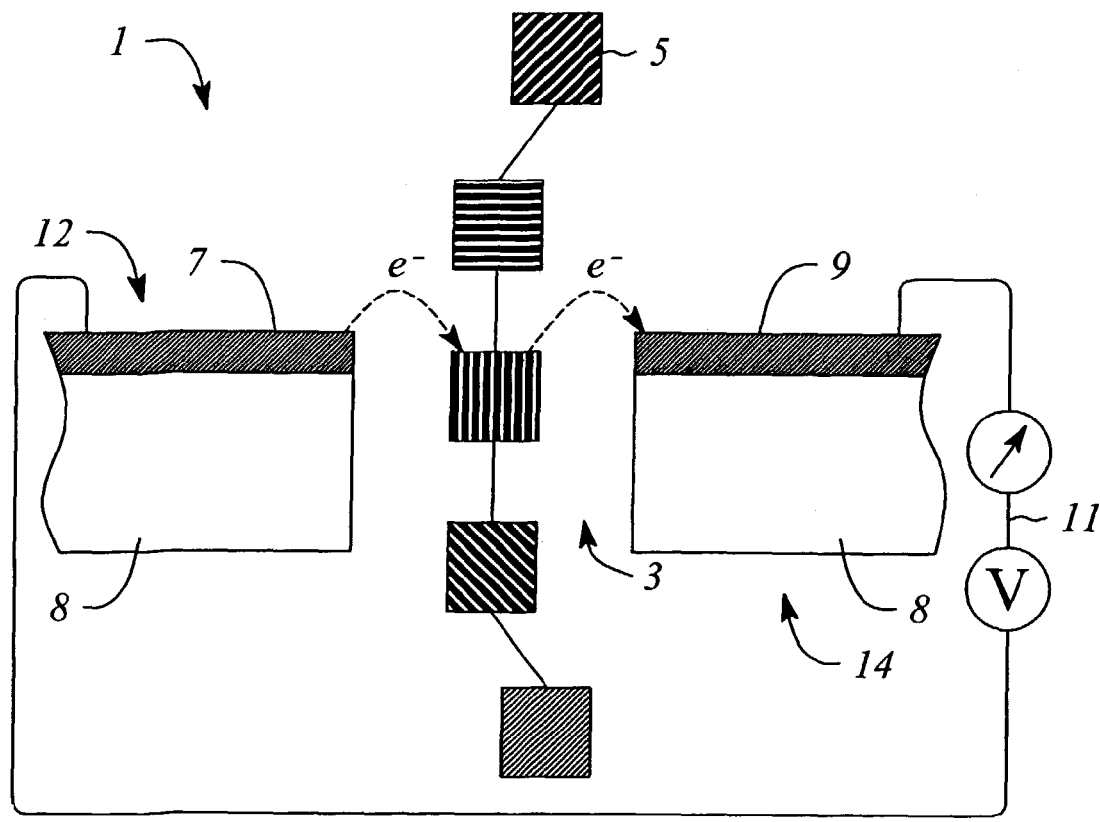
FIG. 3B shows a cross-sectional view of the third embodiment of the present invention.

Referring now to FIGS. 3A and 3B, a third embodiment of the present invention is provided. In this embodiment, the first electrode 7 and the second electrode 9 are spaced in the same plane. One or more optional substrates or electrodes may be employed. When the optional substrate 8 is not employed, the first electrode 7 and the second electrode 9 may be positioned adjacent to define the nanopore 3. Although the figures show a pair of electrodes, the invention should not be interpreted to be limited to only this configuration. Various electrodes of varying shapes or sizes may be employed. Furthermore, it is anticipated that the invention comprises a number of similar or different electrodes capable of tunneling in a variety of directions and space (i.e. one, two and three dimensional space).

Having described the important components of the invention, a brief description of the voltage gradient and scanning of the electronic energy levels is in order. An important component of the invention is the potential means 11. As described above, the potential means 11 may be ramped. The purpose of the ramping and how it is accomplished will now be discussed.

While it is possible to imagine some differences in the tunneling current due to the size and general characteristics of a translocating monomer in the region between two conducting electrodes as illustrated in FIGS. 1-3, it would be naively expected that the tunneling currents for each monomer would have qualitatively similar magnitudes, making differentiating the various monomers problematic. This is particularly true when it is considered that the biopolymer will move about laterally as it passes through the pore, significantly changing the magnitude of the tunneling current. Instead, it is proposed that to adequately differentiate the monomers, it is necessary to identify the internal structure of each individual monomer. This would be most readily accomplished by "scanning" the electronic energy level structure of each monomer as it translocates the pore. First, the physical mechanism by which it can be accomplished is described, making clear the dynamical requirements. Then, a physical realization of a structure that satisfies these requirements will be given.

Figure 4:
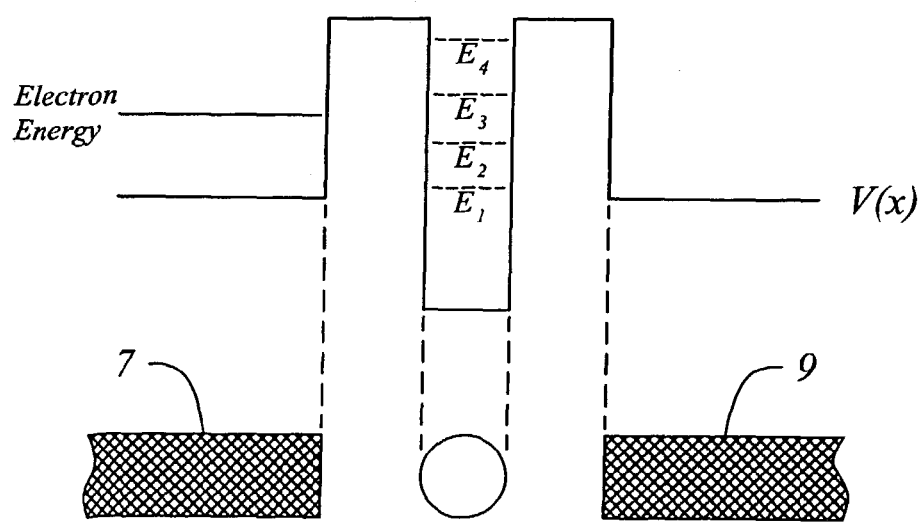
FIG. 4 shows a simple one-dimensional quantum mechanical potential model of the physical electrode nanopore system.

It is important to have a simple model physical system that exhibits the relevant characteristics of the real system, yet is tractable. FIG. 4 shows a model of a tunneling configuration. It is a one dimensional quantum mechanical representation of the physical system, where the potential energy levels are chosen to represent the identified physical regions as shown. While the detailed shapes of the barriers and quantum well corresponding to the monomer are not important, the general characteristic of a quantum well with a distinct energy level spectrum that is separated by energy barriers from the conduction electrodes is important.

Figure 5:
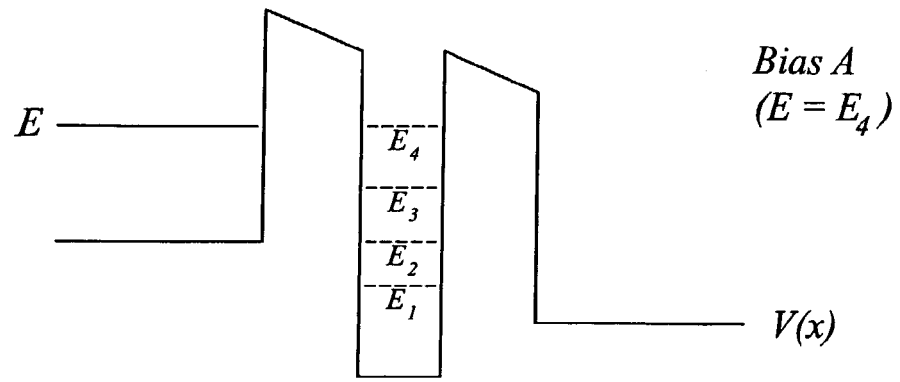
FIG. 5 shows a schematic representation of resonant tunneling conditions for the one-dimensional double-barrier quantum mechanical model.
Figure 5:
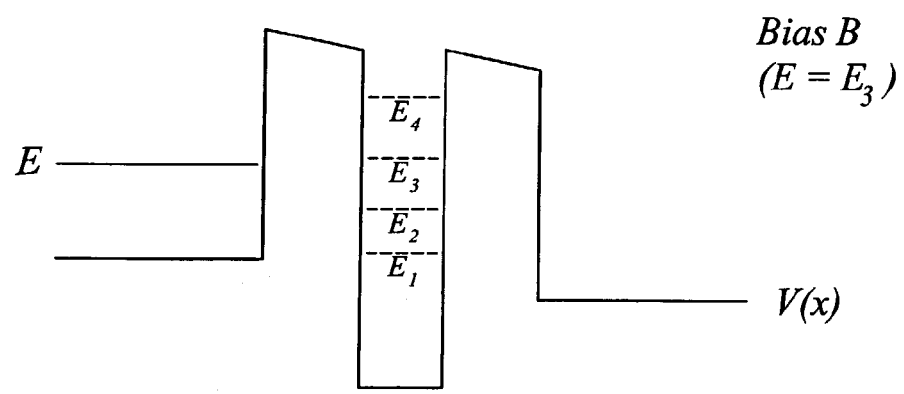
Figure 5:
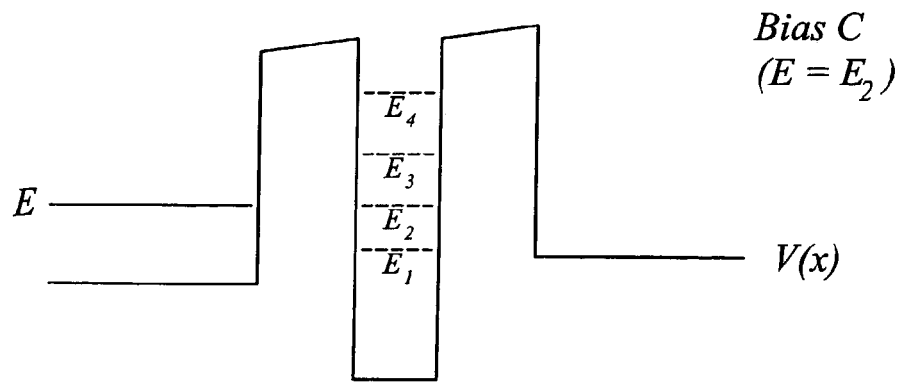

It is well known from quantum mechanical calculations, that for the double barrier potential shown in FIG. 4, the transmission probability of a particle incident upon this structure is 100% if the incident energy matches one of the bound state energies of the central quantum well (some crucial additional factors regarding the barriers must also be satisfied, and this will be discussed in detail later). This phenomenon is called resonant tunneling, and is a central feature of the present invention. The general idea employed in the present invention is to ramp the tunneling voltage across the electrodes over the energy spectrum of the translocating biopolymer 5. As shown in FIG. 5, at specific voltages the incident energy will sequentially match the internal nucleotide energy levels, giving rise to enormous increases in the tunneling current. It is, of course, necessary that the ramp-time of the applied voltage is short compared to the nucleotide translocation time through the nanopore. Under current experimental conditions, the monomers translocate the nanopore in roughly a microsecond (See Kasianowicz et al., "Characterization of individual polynucleotide molecules using a membrane channel", *Proc. Natl. Acad. Sci. USA*, 93: 13770-13773, 1996; Akeson et al., "Microsecond time-scale discrimination among polycytidylic acid, polyadenylic acid, and polyuridylic acid as homopolymers or as segments within single RNA molecules", Biophys. J. 77: 3227-3233 (1999)). Thus, the constraint placed upon the applied tunneling voltage frequency is that it be something in excess of about 10 MHz.

A detailed study of the one-dimensional quantum mechanical double-barrier transmission problem reveals a severe difficulty with the above measurement scenario. In the Appendix, the transmission problem is solved exactly, and it is shown that the transmission probability only becomes 100% when the incident energy matches an internal energy level and the two barriers are of equal strength. This "equal barrier condition" is documented in the literature, but rarely mentioned in discussions of resonant tunneling phenomena. To make the discussion quantitiative and explicit, it is noted that for the double-barrier structure depicted in FIG. 4, the non-resonant tunneling probability has the form:

$$T_{tot} \sim T_L \cdot T_R \qquad (1)$$

Where $T_L$ ($T_R$) is the quantum mechanical tunneling probability through the left (right) barrier. These tunneling factors depend exponentially upon the integrated strength of the individual barriers $$T_i \sim e^{-2K_i L} \quad (2)$$

where $$K_i = \sqrt{\frac{2\mu(V_i - E)}{\hbar}} \quad (3)$$

L is the barrier width, $\mu$ is the carrier mass, and ($V_i$-E) is the energy difference between the top of the barrier and the incident energy. (As an order of magnitude estimate, it can be assumed that a single barrier height is roughly 2.5 eV and the single barrier width is about 0.5 nm for the current nanopore structures, giving a single-barrier tunneling probability $T_i \sim 3 \times 10^{-4}$). These small tunneling probabilities are clearly the limiting factors in the determination of the magnitude of the tunneling currents.

A remarkable property of the double-barrier structure is that there can be an enormous enhancement of the transmission probability, and thus tunneling current, when the energy of the incident particle matches the energy of a bound state of the central quantum well. In fact, for certain conditions, the transmission probability becomes unity regardless of the magnitude of the barriers surrounding the well. This phenomenon is called resonant tunneling. As shown in the Appendix, the total transmission probability for the general double-barrier structure has the form $$T_{tot} \sim \frac{1}{\left[\frac{A(E)}{T_L T_R} + B(E)\frac{T_L}{T_R} + C(E)\frac{T_R}{T_L} + D(E)T_R T_L\right]} \quad (4)$$

where A, B, C, D are factors that are of order unity and depend weakly upon the energy, E. For general non-resonant tunneling, it is assumed that $T_L$ and $T_R$ are much less than unity and thus the expression for the total transmission probability is dominated by the first term in the denominator of the equation (4) yielding $$T_{tot} \sim T_L \cdot T_R \quad (5)$$

as previously stated. Resonant tunneling corresponds to the situation where the energy matches an internal energy level of the central quantum well. When this is the case, as shown in the Appendix, the coefficient A(E) vanishes, indicating that the behavior of the total transmission coefficient expressed in equation (4) will now be dominated by a non-leading term. It is clearly seen that if $T_L = T_R$, i.e. the barriers are of equal integrated magnitudes, the total transmission probability is of order unity. In fact, it can be shown from the expressions in the Appendix, that for equal barriers on resonance $$T_{tot} = 1. \quad (6)$$

However, even though the energy may be chosen to match an internal energy level, which drives the coefficient A(E) to zero, if the barriers are not of equal magnitude, the transmission coefficient remains small. For specificity, assume that $T_L \ll T_R$. Then, from equation (4), it is seen that the total transmission is given by $$T_{tot} \sim \frac{T_L}{T_R} \quad (7)$$

that is clearly much less than one even on resonance. Similarly, for a situation where $T_R \ll T_L$, the dominant term from the equation (4) takes the form $$T_{tot} \sim \frac{T_R}{T_L}. \quad (8)$$

Thus, the previously described approach of scanning the tunneling voltage and measuring large resonant tunneling currents corresponding to the spectrum of the sequential translocating monomers is problematic. In particular, for the situation where the translocating biopolymer through the nanopore is away from the nanopore's center position, or is oriented in such a fashion that the steric asymmetries cause the two tunneling barriers to be unequal, the two constituent tunneling probabilities $T_L$ and $T_R$ are of greatly different magnitudes due to the exponential dependence of the tunneling probabilities on the barrier magnitudes. For this condition, as can be seen from the equations (7) and (8), the gain in transmission probability and thus tunneling current is small indeed.

The solution to this problem is embodied in the structure schematically shown in FIGS. 1-3. These structures take advantage of the fact that the biopolymer 5 is in motion through the nanopore. As a monomer translocates through the nanopore and between the two ring electrodes, it will always pass a point where the barriers separating it from the two ring electrodes are equal, regardless of the origin of the initial barrier asymmetry (either spatial separation or steric asymmetry). At this point, there will be large resonant tunneling current increases as the tunneling voltage scans the internal energy spectrum of the individual monomer. A representative plot of an expected resonant tunneling current output spectrum is shown in FIG. 5 as a function of time, alongside the applied tunneling electrode voltage, for reference. As previously stated, each type of monomer would have a characteristic internal energy level spectrum which would allow it to be distinguished from the other monomer types.

The embodiments of the ring electrode structure shown in FIGS. 1-3 are merely illustrative, and not intended to limit the scope of the present invention. For ease of fabrication, any fraction of the upper and lower surfaces could in fact be metallized, as long as the entire region surrounding the opening of the nanopore is metallized. This would obviate the need for precise alignment and placement of lithographically defined metal electrode structures.

Figure 6:
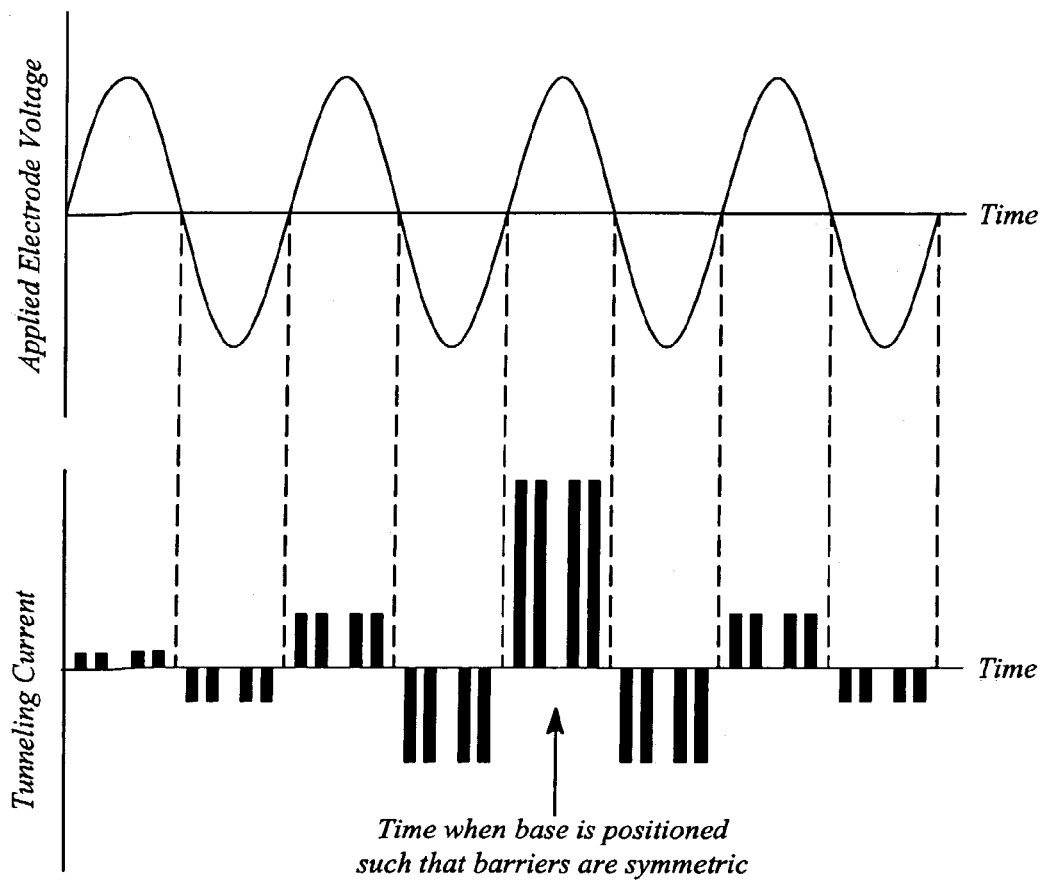
FIG. 6 shows a representative plot of an expected resonant tunneling current spectrum as a function of time (alongside the applied tunneling electrode voltage for reference).

Referring now to FIG. 6, the applied voltage and tunneling current can be seen to produce a defined signal that is indicative of the portion of the biopolymer 5 that is proximal to the first electrode 7, or the second electrode 9. Each nucleotide base or portion of biopolymer 5 should produce a differing signal in the tunneling current over time as the varying voltage is applied. For instance, when the monomer or portion of biopolymer 5 is positioned such that the barriers are symmetric, a larger overall signal can be seen from the tunneling current. These differing signals provide a spectrum of the portion of the biopolymer 5 that is positioned proximal to the first electrode 7, or the second electrode 9. These spectra can then be compared by computer to previous spectra or "finger prints" of nucleotides or portions of biopolymer 5 that have already been recorded. The nucleotide or portion of biopolymer 5 can then be determined by comparison to this database. This data and information can then be stored and supplied as output data of a final sequence.

Having now described the apparatus of the invention in detail, a discussion of the method is now in order. The method of the present invention provides a means for identifying or sequencing the biopolymer 5 that is located in the nanopore 3 defined between the first electrode 7 and the second electrode 9. The method comprises the step of applying an electrical current from the first electrode 7 through a portion of the biopolymer 5 to the second electrode 9 to identify the portion of the biopolymer 5 positioned in the nanopore 3. The biopolymer 5 may be identified by the change in the tunneling current at various stages of the applied electrode voltage. In addition, the method of the present invention provides a potential means 11 for ramping a voltage or potential from the first electrode 7 through a portion of a biopolymer 5 to the second electrode 9 to scan energy levels until the energy levels of the first electrode 7, the biopolymer 5 and the second electrode 9 are on resonance. The ramping potential is applied to identify the portion of the biopolymer 5 positioned in the nanopore 3.

EXAMPLE 1

The device can be fabricated using various techniques and materials. The nanopore can be made in a thin (500 nM) freestanding silicon nitride (SiN3) membrane supported on a silicon frame. Using a Focused Ion Beam (FIB) machine, a single initial pore of roughly 500 nM diameter can be created in the membrane. Then, illumination of the pore region with a beam of 3 KeV Argon ions sputters material and slowly closes the hole to the desired dimension of roughly 2 nM in diameter (See Li et al., "Ion beam sculpting at nanometer length scales", *Nature,* 412: 166-169, 2001). Metal electrodes are formed by evaporation or other deposition means on the opposing surfaces of the SiN3 membrane. Wire bonding to the metal electrodes allows connection to the tunneling current bias and detection system. The bias is applied using an AC source with the modest requirement of roughly 3-5 volts at 30-50 MHz. The tunneling currents are expected to be in the nanoamp range, and can be measured using a commercially available patch-clamp amplifier and head-stage (Axopatch 200B and CV203BU, Axon Instruments, Foster City, Calif.).

APPENDIX

Figure 7:
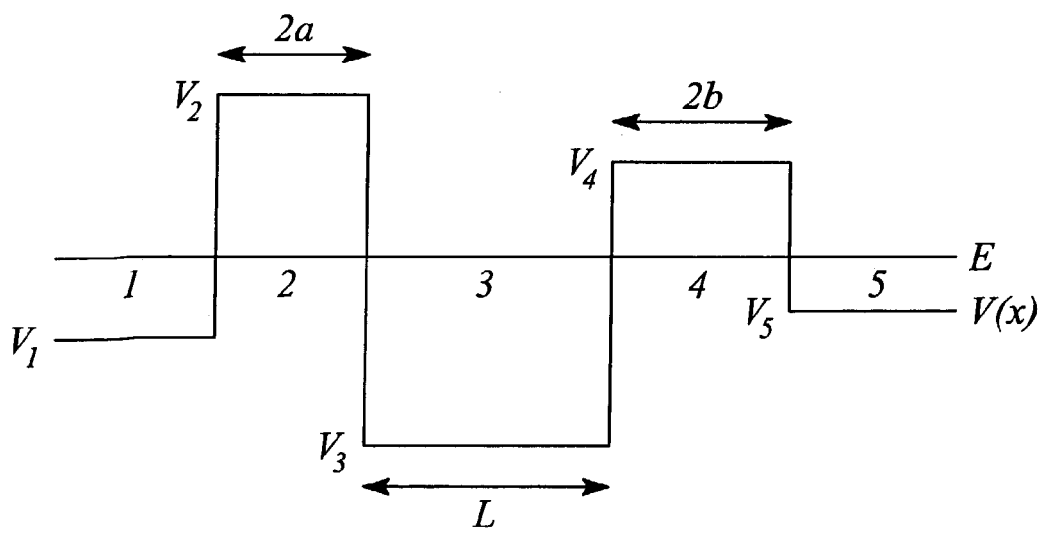
FIG. 7 shows a model one dimensional quantum mechanical double-barrier structure to be analyzed, with relevant parameters defined.

The model physical system to be analyzed is a one-dimensional quantum mechanical double-barrier structure shown in FIG. 4. The structure is analyzed by solving the time-independent Schrödinger equation for a fixed energy incident particle, and computing the transmission probability. The parameters used in the calculations are defined in FIG. 7.

A1. Double Barrier Solution

It is assumed that the particle total energy is greater than the potential energy in all regions except the barriers. Under this condition, the solutions to the Schrödinger equation in each of the five regions defined in FIG. 7 can be written down directly $$\Psi_1 = A_1 e^{ik_1 x} + B_1 e^{-ik_1 x} \qquad 1(A1)$$

$$\Psi_2 = A_2 e^{-k_2 x} + B_2 e^{k_2 x} \qquad 1(A2)$$

$$\Psi_3 = A_3 e^{ik_3 x} + B_3 e^{-ik_3 x} \qquad 1(A3)$$

$$\Psi_4 = A_4 e^{-k_4 x} + B_4 e^{k_4 x} \qquad 1(A4)$$

$$\Psi_5 = A_5 e^{ik_5 x} + B_5 e^{-ik_5 x} \qquad 1(A5)$$

where $$\hbar k_{1,3,5} = \sqrt{2\mu(E - V_{1,3,5})} \qquad 1(A6)$$

-continued $$\hbar k_{2,4} = \sqrt{2\mu(V_{2,4} - E)}. \qquad 1(A7)$$

The solution is determined by matching $\psi$ and $d\psi/dx$ at the interfaces of all the homogenous regions. This procedure can be performed as a pair of subproblems. Matching the boundary conditions across the first barrier allows the wavefunction coefficient in region 1 to be written in terms of the coefficients in region 3

$$\begin{pmatrix} A_1 \\ B_1 \end{pmatrix} = \begin{pmatrix} M_{11} & M_{12} \\ M_{21} & M_{22} \end{pmatrix} \begin{pmatrix} A_3 \\ B_3 \end{pmatrix} \qquad 1(A8)$$

where $$M_{11} = \frac{-i(k_1^2 + k_2^2)^{1/2}(k_2^2 + k_3^2)^{1/2}}{4k_1 k_2} \qquad 1(A9)$$

$$e^{i(k_1 + k_3)a}(e^{2k_2 a + i(\phi_2 + \phi_3)} - e^{-2k_2 a - i(\phi_2 + \phi_3)})$$

$$M_{12} = \frac{-i(k_1^2 + k_2^2)^{1/2}(k_2^2 + k_3^2)^{1/2}}{4k_1 k_2} \qquad 1(A10)$$

$$e^{i(k_1 - k_3)a}(-e^{2k_2 a + i(\phi_2 - \phi_3)} + e^{-2k_2 a - i(\phi_2 - \phi_3)})$$

$$M_{22} = M_{11}^* \qquad 1(A11)$$

$$M_{21} = M_{12}^* \qquad 1(A12)$$

and $$\phi_2 \equiv a\tan(k_2/k_1) \qquad 1(A13)$$

$$\phi_3 \equiv a\tan(k_2/k_3). \qquad 1(A14)$$

Similarly, matching the boundary conditions across the second barrier allows the wavefunction coefficients in region 3 to be written in terms of the coefficients in region 5

$$\begin{pmatrix} A_3 \\ B_3 \end{pmatrix} = \begin{pmatrix} N_{11} & N_{12} \\ N_{21} & N_{22} \end{pmatrix} \begin{pmatrix} A_5 \\ B_5 \end{pmatrix} \qquad 1(A15)$$

where $$N_{11} = \frac{-i(k_3^2 + k_4^2)^{1/2}(k_4^2 + k_5^2)^{1/2}}{4k_3 k_4} \qquad 1(A16)$$

$$e^{-ik_3(a+L)+ik_5 b}(e^{2k_4 b + i(\phi_4 + \phi_5)} - e^{-2k_4 b - i(\phi_4 + \phi_5)})$$

$$N_{12} = \frac{-i(k_3^2 + k_4^2)^{1/2}(k_4^2 + k_5^2)^{1/2}}{4k_3 k_4} \qquad 1(A17)$$

$$e^{-ik_3(a+L)-ik_5 b}(-e^{2k_4 b + i(\phi_4 - \phi_5)} + e^{-2k_4 b - i(\phi_4 - \phi_5)})$$

$$N_{22} = N_{11}^* \qquad 1(A18)$$

$$N_{21} = N_{12}^* \qquad 1(A19)$$

and $$\phi_4 \equiv a\tan(k_4/k_3) \qquad 1(A20)$$

$$\phi_5 \equiv a\tan(k_4/k_5). \qquad 1(A21)$$

The full expression connecting the wavefunction coefficients of region 1 with those of region 5 is determined by concatenating the matrices of equations (A8) and $$\begin{pmatrix} A_1 \\ B_1 \end{pmatrix} = \begin{pmatrix} M_{11} & M_{12} \\ M_{21} & M_{22} \end{pmatrix} \begin{pmatrix} N_{11} & N_{12} \\ N_{21} & N_{22} \end{pmatrix} \begin{pmatrix} A_5 \\ B_5 \end{pmatrix}. \quad 1(A22)$$

The full transmission coefficient is determined by applying the boundary condition $$\begin{pmatrix} A_1 = 1 \\ B_1 \end{pmatrix} = \begin{pmatrix} M_{11} & M_{12} \\ M_{21} & M_{22} \end{pmatrix} \begin{pmatrix} N_{11} & N_{12} \\ N_{21} & N_{22} \end{pmatrix} \begin{pmatrix} A_5 \\ B_5 = 0 \end{pmatrix} \quad 1(A23)$$

which corresponds to an incident wave of unit amplitude from the left ($A_1$=1) and no wave incident from the right ($B_5$=0). Thus the calculated probability flux transmission is given by $$T_{tot} = \frac{k_5}{k_1} \left| \frac{1}{M_{11}N_{11} + M_{12}N_{21}} \right|^2. \quad 1(A24)$$

Performing the required algebra to explicitly evaluate equation (A24), and collecting and grouping terms which are listed in descending powers of the large "barrier suppression factors"

$$T_{tot} = \frac{2^6 k_1 k_2^2 k_3^2 k_4^2 k_5}{(k_1^2 + k_2^2)(k_2^2 + k_3^2)(k_3^2 + k_4^2)(k_4^2 + k_5^2)} \frac{1}{F} \quad 1(A25)$$

where $$F = e^{2\gamma_2 + 2\gamma_4} \sin^2(\phi_1 - \phi_3 - \phi_4) \quad 1(A26)$$
$$+ e^{2\gamma_2} \cos(2\phi_5)(-\cos(2\phi_4) + \cos(2\phi_1 - 2\phi_3))$$
$$+ e^{2\gamma_4} \cos(2\phi_2)(-\cos(2\phi_3) + \cos(2\phi_1 - 2\phi_4))$$
$$+ e^{2\gamma_2 - 2\gamma_4} \sin^2(\phi_1 - \phi_3 + \phi_4)$$
$$+ e^{2\gamma_4 - 2\gamma_2} \sin^2(\phi_1 + \phi_3 - \phi_4)$$
$$+ e^0 \cos(2\phi_2 - 2\phi_5)(-\cos(2\phi_1) + \cos(2\phi_3 - 2\phi_4))$$
$$+ e^0 \cos(2\phi_2 + 2\phi_5)(-\cos(2\phi_1) + \cos(2\phi_3 + 2\phi_4))$$
$$+ e^{-2\gamma_4} \cos(2\phi_2)(-\cos(2\phi_3) + \cos(2\phi_1 + 2\phi_4))$$
$$+ e^{-2\gamma_2} \cos(2\phi_5)(-\cos(2\phi_4) + \cos(2\phi_1 + 2\phi_3))$$
$$+ e^{-2\gamma_2 - 2\gamma_4} \sin^2(\phi_1 + \phi_3 + \phi_4)$$

and the following definitions have been used for notational simplicity $$\phi_1 \equiv k_3 L \quad 1(A27)$$

$$\gamma_2 \equiv 2k_2 a \quad 1(A28)$$

$$\gamma_4 \equiv 2k_4 b. \quad 1(A29)$$

A2. Resonance Condition

Assuming the barriers are strong impediments to particle transmission, i.e. $e^{2\gamma_2}$, $e^{2\gamma_4} \gg 1$, for general "non-resonant" conditions the total transmission is dominated by the first term in equation (A26), yielding $$T_{tot} \sim e^{-2\gamma_2 - 2\gamma_4} \sim T_L T_R. \quad 1(A30)$$

For this case, the total transmission is proportional to the product of the transmissions of the two barriers separately. However, for the particular situation that $$\phi_1 - \phi_3 - \phi_4 = n\pi, \quad 1(A31)$$

the coefficients of the first three terms in equation (A26) vanish. If the two barriers are of equal integrated magnitudes, i.e., $\gamma_2 = \gamma_4$, then the leading term in equation (A26) is of order $e^0 \sim 1$, and the total transmission coefficient can be shown to approach 1. This is the condition called resonant tunneling, and exhibits the remarkable property of total transmission through a double-barrier structure, regardless of the strengths of the individual barriers (as long as they are equal).

It is important to understand the physical significance of the so-called resonance condition stated in equation (A31). For ease of analyzing this condition, we will restrict our attention to the completely symmetric case $$\phi_3 = a \tan(k_2/k_3) = a \tan(k_4/k_3) = \phi_4 \quad 1(A32)$$

leading to $$\sin(\phi_1 - 2\phi_3) = 0. \quad 1(A33)$$

Applying simple trigonometric identities, and inserting the definitions of $\Phi_1$ and $\Phi_3$, equation (A33) can be rewritten as $$\tan(k_3 L) = \frac{\sqrt{V_2 - E}\sqrt{E - V_3}}{E - (V_2 + V_3)/2}. \quad 1(A34)$$

If the arbitrary baseline potential energy level is chosen as $V_3 \equiv 0$, and $V_2$ is renamed $V_0$, equation (A34) take the form $$\tan(k_3 L) = \frac{\sqrt{V_0 - E}\sqrt{E}}{E - V_0/2}. \quad 1(A35)$$

It is recognized that this condition is precisely the eigenvalue equation for the energy levels of a square well potential with the parameters stated above (See Landau and Lifshitz, "Quantum Mechanics", Pergamon, Oxford (1989)). This demonstrates why this phenomenon of total transmission through the double-well structure is called resonant tunneling. The condition of resonant tunneling is precisely that the energy of the incident particle must match the resonant energy of the central potential well. Whenever the incident energy matches any of the resonant energies, the total particle transmission increases dramatically, as long as the double-barriers are symmetric.

A3. Tunneling Current on Resonance

As described above, for a symmetric potential structure, the transmission probability becomes unity when the incident particle energy passes through a resonance of the central well. However, the situation is markedly different for a double-barrier structure that has asymmetric barriers. For the general asymmetric structure on resonance, it is seen from equation (A26) that the leading behavior has the form $$F \sim e^{2\gamma_2 - 2\gamma_4} \sin^2(\phi_1 - \phi_3 + \phi_4) + e^{2\gamma_4 - 2\gamma_2} \sin^2(\phi_1 + \phi_3 - \phi_4). \quad 1(A36)$$

This implies that for the situation where the left barrier is larger ($\gamma_2 \gg \gamma_4$)

$$T_{tot} \sim e^{2\gamma_4 - 2\gamma_2} \sim \frac{T_L}{T_R} \qquad 1(A37)$$

and for the situation where the right barrier is larger ($\gamma_4 \gg \gamma_2$)

$$T_{tot} \sim e^{2\gamma_2 - 2\gamma_4} \sim \frac{T_R}{T_L}. \qquad 1(A38)$$

This demonstrates the markedly different resonant tunneling behavior for the asymmetric double-barrier structure. If the barrier is highly asymmetric, there is very little gain in the tunneling probability as the resonance condition is approached. It is only under the condition of double-barrier symmetry that the resonant tunneling phenomenon of barrier transparency is in effect.

I claim:

1. An apparatus for detecting a biopolymer in a nanopore, comprising:
   (a) a first electrode;
   (b) a second electrode adjacent to said first electrode;
   (c) a nanopore adjacent to said first electrode and said second electrode and positioned to allow said biopolymer to be positioned between said first electrode and said second electrode; and
   (d) potential means for electrically connecting said first electrode and said second electrode for applying a ramping voltage over an energy spectrum of the biopolymer from said first electrode, through a portion of said biopolymer in said nanopore, to said second electrode to produce a signal indicative of said portion of said biopolymer;
   wherein ramp-time of the applied voltage is short compared to a nucleotide translocation time through the nanopore.

2. The apparatus of claim 1, wherein the first and second electrodes are ring electrodes, the apparatus further comprising a substrate for positioning said first electrode and said second electrode.

3. The apparatus of claim 1, further comprising at least a first substrate for positioning said first electrode.

4. The apparatus of claim 1, further comprising at least a second substrate for positioning said second electrode.

5. The apparatus of claim 1, further comprising at least a first substrate for positioning a nanopore.

6. The apparatus of claim 1, further comprising a means for signal detection for detecting said signal produced from said portion of said biopolymer.

7. The apparatus of claim 1, wherein said biopolymer is a charged polymer.

8. The apparatus of claim 6, wherein said biopolymer is selected from the group consisting of carbohydrates, proteins, nucleic acids, lipids, glycans, polynucleotides, proteoglycans and polypeptides.

9. A method for identifying a biopolymer translocating through a nanopore, comprising:
   (a) applying a ramping voltage over an energy spectrum of the biopolymer from a first electrode through a portion of said biopolymer to a second electrode to identify said portion of said biopolymer positioned in said nanopore;
   wherein ramp-time of the applied voltage is short compared to a nucleotide translocation time through the nanopore.

10. The method of claim 9, wherein said ramping voltage produces an electrical current, and wherein said electrical current is a tunneling current with an energy level that matches at least one conduction band energy of a portion of said biopolymer.

11. The method of claim 10, wherein said tunneling current is in resonance with said conduction band energies of a portion of said biopolymer.

12. The method of claim 9, further comprising translocating said biopolymer through said nanopore to identify each of said translocating portions of said biopolymer.

13. An apparatus for detecting a biopolymer translocating a nanopore, comprising:
   (a) a first electrode having a first nanopore;
   (b) a second electrode adjacent to said first electrode having a second nanopore wherein said first nanopore of said first electrode is positioned with said second nanopore of said second electrode so that said biopolymer may translocate through said first nanopore and said second nanopore; and
   (c) potential means for electrically connecting said first electrode and said second electrode for applying a ramping voltage over an energy spectrum of the biopolymer from said first electrode through a portion of said biopolymer to said second electrode to produce a detectable signal indicative of a portion of said biopolymer translocating said first nanopore and said second nanopore;
   wherein ramp-time of the applied voltage is short compared to a nucleotide translocation time through the nanopore.

14. The apparatus of claim 13, wherein the center point of said nanopore of said first electrode is positioned coaxially with the center point of said nanopore of said second electrode.

15. The apparatus of claim 14, wherein said first electrode is positioned above said second electrode.

16. The apparatus of claim 13, further comprising a substrate for positioning said first electrode and said second electrode.

17. The apparatus of claim 13, further comprising at least a first substrate for positioning said first electrode.

18. The apparatus of claim 13, further comprising at least a second substrate for positioning said second electrode.

19. An apparatus for detecting a portion of a biopolymer translocating a nanopore, comprising:
   (a) a first electrode;
   (b) a second electrode spaced from said first electrode to define a nanopore between said first electrode and said second electrode, said nanopore designed for receiving a translocating biopolymer, said first electrode being in electrical connection with said second electrode; and
   (c) potential means for electrically connecting said first electrode and said second electrode for applying a ramping voltage over an energy spectrum of the biopolymer from said first electrode, across said biopolymer to said second electrode to produce a signal indicative of a portion of said biopolymer translocating said nanopore;
   wherein ramp-time of the applied voltage is short compared to a nucleotide translocation time through the nanopore.

20. The apparatus of claim 19, wherein said biopolymer is translocated in a stepwise fashion through said nanopore defined between said first electrode and said second electrode.

21. A method for identifying a biopolymer in a nanopore defined between a first and second electrode, comprising:

applying a ramping voltage over an energy spectrum of the biopolymer from a first electrode through a portion of a biopolymer to a second electrode to scan energy levels until the energy levels of said first electrode, said biopolymer and said second electrode are in resonance, said ramping potential to produce a detectable signal to identify said portion of said biopolymer positioned in said nanopore;

wherein ramp-time of the applied voltage is short compared to a nucleotide translocation time through the nanopore.

22. The method of claim 21, wherein monomers of the biopolymer comprise a quantum well comprising an identifiable energy level spectrum that is separated by energy barriers from the electrodes.

23. An apparatus for detecting a biopolymer in a nanopore, comprising:
   (a) a first electrode;
   (b) a second electrode adjacent to said first electrode;
   (c) a nanopore adjacent to said first electrode and said second electrode and positioned to allow said biopolymer to be positioned between said first electrode and said second electrode; and
   (d) potential means for electrically connecting said first electrode and said second electrode for applying a ramping voltage over an energy spectrum of the biopolymer from said first electrode, through a portion of said biopolymer in said nanopore, to said second electrode to produce a signal indicative of said portion of said biopolymer, wherein ramp-time of the applied voltage is short compared to a nucleotide translocation time through the nanopore; and wherein said ramping voltage induces resonant tunneling.

24. The apparatus of claim 23, further comprising at least a first substrate for positioning a nanopore.

25. The apparatus of claim 23, further comprising a means for signal detection for detecting said signal produced from said portion of said biopolymer.

26. A method for identifying a biopolymer translocating through a nanopore, comprising:
   (a) applying a ramping voltage over an energy spectrum of the biopolymer from a first electrode through a portion of said biopolymer to a second electrode to identify said portion of said biopolymer positioned in said nanopore;

wherein ramp-time of the applied voltage is short compared to a nucleotide translocation time through the nanopore; and wherein said ramping voltage induces resonant tunneling.

\* \* \* \* \*